United States Patent [19]

DuVall

[11] Patent Number: 4,688,575

[45] Date of Patent: Aug. 25, 1987

[54] MUSCLE CONTRACTION STIMULATION

[76] Inventor: Wilbur E. DuVall, 12624 Spring Valley Pkwy., Victorville, Calif. 92392

[21] Appl. No.: 357,568

[22] Filed: Mar. 12, 1982

[51] Int. Cl.⁴ .............................................. A61N 1/36
[52] U.S. Cl. .................................... 128/422; 128/788
[58] Field of Search ............................... 128/421–423, 128/788, DIG. 25

[56] References Cited

U.S. PATENT DOCUMENTS

| | | | |
|---|---|---|---|
| 3,241,557 | 3/1966 | Masaki | 128/422 |
| 3,255,753 | 6/1966 | Wing | 128/421 |
| 3,589,370 | 6/1971 | McDonald | 128/422 |
| 3,640,284 | 2/1972 | De Langis | 128/422 |
| 3,800,800 | 4/1974 | Garbe et al. | 128/423 |
| 3,933,147 | 1/1976 | Du Vall et al. | 128/788 |
| 3,938,507 | 2/1976 | Sarnoff et al. | 128/706 |
| 3,983,881 | 10/1976 | Wickham | 128/422 |
| 4,106,511 | 8/1978 | Erlandson | 128/422 |
| 4,324,253 | 4/1982 | Greene et al. | 128/421 |
| 4,372,319 | 2/1983 | Ichinomiya et al. | 128/421 |

FOREIGN PATENT DOCUMENTS 1145749  3/1969  United Kingdom ............... 128/788

Primary Examiner—William E. Kamm

[57] ABSTRACT

An instrument (10) for the treatment of incontinence by exercise of the muscle group that includes the puboccygeous muscle furnishes electrical energy to induce muscle contraction. Energy is provided according to a pre-established exercise program at energizing rings (16, 18) at the forward, insertion section of the instrument. All variables of the exercise program are pre-established by internal electronic circuitry (FIG. 4) except energy level. Control of energy level is left to the user at touch switch elements (20, 22, 24) at the rear of the instrument.

8 Claims, 4 Drawing Figures

U.S. Patent    Aug. 25, 1987    4,688,575
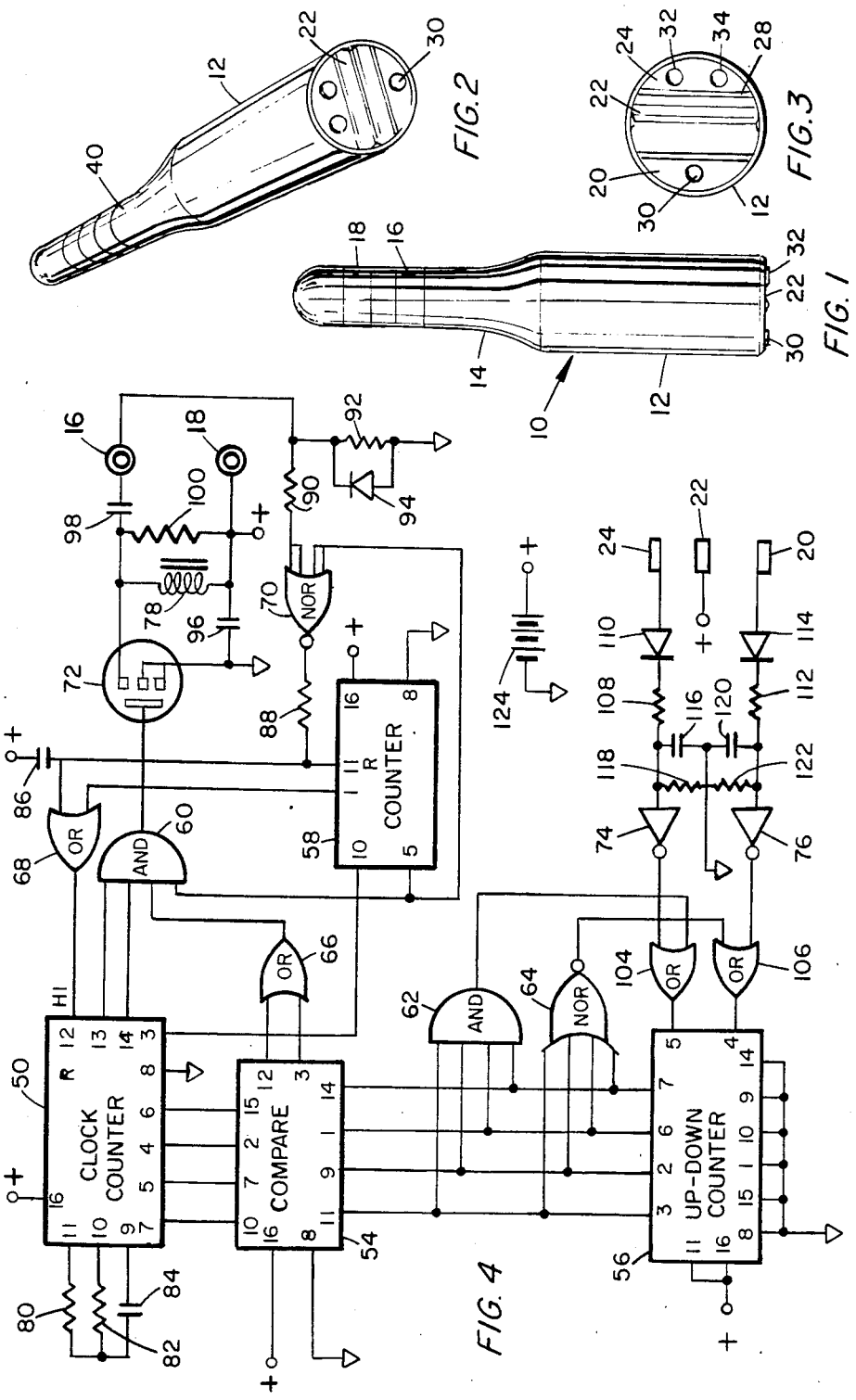

MUSCLE CONTRACTION STIMULATION

TECHNICAL FIELD

This invention relates to methods and apparatus for inducing contraction of muscles and, while not limited thereto, for electronically inducing and controlling the exercise of the muscle group that include the pubococcygeous muscle.

BACKGROUND ART

It was in 1759 that Alessandro Volta established that the twitching of frog legs, observed ten years earlier by Luigi Galvani, was due to an electric current flow. It was probably inevitable that electric current would be applied to humans to accomplish some therapeutic result. A modern application is found in the "pace maker" device which stimulates and controls action of the user's heart muscle. In that application, the function is to induce to action to a muscle that might not otherwise contract. Electrical stimulus can also be used to strengthen or "tone" specific muscles by causing them to contract forcefully, and then to relax, and to repeat that cycle over and over in an exercise program.

One of the most important uses for electrical stimulus in muscle exercise is the strengthening of the puboccygeous and related muscles. Those muscles are disposed in the lower pelvic region of humans, in the vicinity of the bladder and rectum. These muscles are important in control of urinary and fecal discharges, and in maintaining the relative positions of the several organs in the lower pelvic region. A common symptom, indicating inadequate strength in the primary muscle of the group, the puboccygeous, is incontinence in stressful circumstances. Medical research statisticions estimate that thirty percent of the adult female population, and sixty percent of post menopausal women suffer from lack of urinary control. Males, too, have this problem.

A cure for most sufferers can be had by strengthening the muscles of the group in an exercise program. The several muscles can be flexed and relaxed voluntarily whereby the muscles are strengthened in an exercise program involving no more than periodic, voluntary, repetitive contraction of the muscles. However, as in the case of any muscle development effort, it is preferred to increase the intensity of exercise with time, at a rate that is a function of the exerciser's age and weight and starting physical condition.

Intensity is a function of contraction force, duration of contraction, frequency, and number of contractions. Except for number of contractions in each exercise session, regulation of intensity in an exercise program that lasts for a period of several months is not possible when contraction is accomplished voluntarily. As a consequence, physicians who treat incontinence, or otherwise supervise a "p.c." muscle exercise program, prefer that contractions be electrically induced.

DISCLOSURE OF INVENTION

It is an object of the invention to provide the physician, and the patient, with an improved apparatus and method for inducing muscle contraction when the purpose is to strengthen or tone the muscle.

More particularly, it is an object to provide an apparatus by which the several elements of contraction intensity may be varied and controlled.

The most important application of the invention is the treatment to strengthen the "p.c." muscle group. These muscles can be reached for direct electrical stimulation in the patient's rectum or vagina, and the preferred form of the invention is shown in embodiments intended for insertion into one, the vagina, and two, the rectum.

Control of stimulation currents is accomplished in the same fashion in both of those embodiments. It has been discovered that it is best that each exercise session last for some minimum time, whatever the intensity of the exercise is to be. In the preferred form of the invention, an optimum duration is made available by fixing the number of electrical impulses in the series of impulses. In the preferred embodiment, the apparatus senses insertion into a body cavity and begins generation of a given number of impulses each having a fixed duration with successive pulses spaced a fixed duration apart. In the preferred method, pulsing continues for approximately 250 cycles. Each cycle comprises a two-second energization or contraction period, and a two-second off or relaxation period.

In the interest of safety, it is required that the excitation potential, the potential applied to the muscle, be limited. In the preferred embodiment, safety is achieved by fixing the potential at a constant level. Intensity control is achieved by forming each two-second "on" pulse as a sequence of higher, fixed frequency pulse cycles in which the relative duration of "on" and "off" periods can be changed whereby to change the amount of current flow through the muscle. To provide those features is another object of the invention.

The effect of reducing intensity control to a change in the width of individual pulses that make up the contraction inducing pulse train is to provide an instrument which is very simple to use. The patient can use the instrument at home, when convenient, and in complete privacy in exact accordance with the schedule prescribed by the physician.

While the principle objects of the invention are directed to the provision of a greater functional result than has previously been achieved, it is also an object to provide increased utility and to provide such results at reasonable cost. Safety and convenience are enhanced by the use of batteries in lieu of "house current." To insure that batteries are not depleted by failure to operate the power switch, the preferred embodiment employs electronic components, such, for example, as CMOS solid state devices in which quiescent current drain is negligible. That is coupled with a means for sensing whether the instrument's electrodes are or are not positioned within a body cavity and automatically energizing the instrument only when in position for use. No mechanical switching is employed. Off/on switching and pulse width control switching are controlled by resistance or capacitance sensing. It is entirely practical and, indeed, in the preferred instrument, the battery is sealed in place and need not be replaced. The result is an instrument which can be completely immersed in soap and water for cleaning, and one that has no moving parts to fail.

These and other objects and advantages and features of the invention will be more easily understood upon a reading of the description that follows in conjunction with examination of the drawings.

BRIEF DESCRIPTION OF DRAWINGS

In the drawings:

FIG. 1 is a side view of an instrument according to the invention which is designed for insertion into the vagina;

FIG. 2 is a perspective view showing the rectal form of the instrument;

FIG. 3 is an elevational view which depicts the appearance of the rearward, control end of both instruments; and FIG. 4 is a schematic diagram of the electronic circuitry that is employed in the instruments of FIGS. 1 and 2.

DESCRIPTION OF PREFERRED EMBODIMENT

The unit 10, shown in FIG. 1, is the vaginal access version of the exerciser. The rearward portion 12 houses an operating battery and the electronic circuitry. depicted in FIG. 4. It is approximately 5 cm in diameter and 7 cm long. The forward portion 14 is about 2½ cm in diameter and 11 cm long. Except for metal surfaces which are exposed at the rear face of the instrument, and the metal rings 16 and 18 which encompass the forward end 14 of the unit, the exterior of the instrument (its casing) is formed of the non-toxic plastic which is readily cleaned. When the instrument is being used a potential difference appears between the metallic rings 16 and 18. Current flowing between the rings through a path formed by the muscle tissue induces the muscle to contract. In this preferred embodiment, the rings are about 2 cm wide and are spaced approximately ½ apart. The instrument shown in FIG. 2 is the rectal access unit. Except that its forward ringed portion 40 is only about 1 cm in diameter, the two instruments are the same.

At the rearward end of the units, as best shown in FIG. 3, the surface is divided into three metallic areas designated 20, 22 and 24, respectively. The areas 20 and 22 are electrically insulated from one another by a bar 26 of insulating material that extends between them and, at the margins of the case, by the plastic of the wall 12. Similarly, areas 22 and 24 are electrically insulated one from the other by a bar 28 of insulating material and, at the margins of the instrument, by the non-conducting plastic wall 12. Placing a finger so that it bridges the bar 26 and touches the areas 20 and 22 simultaneously results in a switching action to be described later. Bridging the insulating bar 28 by placing a finger so that it touches both the regions 22 and 24 accomplishes a different switching action. It, too, will be explained below in connection with the description of operation of FIG. 4.

A small protrusion, or boss, 30 which extends rearwardly from the surface 20 distinguishes surface 20 from surface 24 which has two such protrusions, or bosses, numbered 32 and 34 respectively. The user, by feeling those protrusions, can determine which of the two switch actions is being accomplished when the insulating bars are bridged. In the embodiment selected for illustration here, bridging the insulating bar 26 by contacting the metal surfaces 20 and 22 simultaneously has the effect of switching the internal circuitry in a direction to decrease energy flow to the muscle whereto to decrease the degree of its contraction. Conversely, touching the metal areas 22 and 24 simultaneously results in a switching action that increases the amount of energy flow between the rings 16 and 18. The amount of energy available to flow through the muscle, between the rings, can be increased in a series of fifteen steps, and, similarly, can be reduced through a series of fifteen steps.

The rings 16 and 18 serve not only to supply energy to the muscle to be exercised, but serve also to sense when the instrument has been positioned in the body cavity. Removed from use, the resistance between the rings is very high. When the instrument is in place, the tissue overlying the rings presents a reduced resistance. The instrument senses that and turns on that portion of the instrument which supplies the contraction inducing energy to the rings. Inserting the instrument into the body cavity is said to turn the instrument on. Removing it from the cavity will return the instrument off.

That portion of the electronic circuitry which controls the amount of energy that is supplied to the metal rings is not turned off. Because of that, the energy level to be supplied at the rings can be preset without turning the instrument on. Moreover, the instrument will remember the setting, whether the energy delivery portion of the unit is turned on or off.

Maximum contraction of the muscles is achieved with an energy level so low that no safety hazard is imposed. To ensure that no failure can result in the release of a harmful amount of energy, the preferred embodiment uses rechargeable batteries which are permanently installed. The use of CMOS or similar solid state technology results in quiescent current drains that are miniscule. It is practical and, in the preferred embodiment, the battery is built in and need not and cannot be changed by the user.

It has been discovered that the optimum period for maintaining contraction is about two seconds, followed by a two-second period of relaxation. Below 1¾ seconds, the exercise is less beneficial, and above 2¼ seconds, it tends to become tiring when continued for more than a few minutes. Experimentation has demonstrated that a pulse cycle in which the off and on times are substantially equal provides the best result and is the least tiring. Contraction and relaxation are not instantaneous. If the off period is too short, the muscle will not be fully relaxed, and the exercising will be both less effective and will be tiring. When the off period is extended much beyond two seconds, the exercise period becomes unduly protracted. It has been discovered that the optimum number of cycles in an exercise period is approximately 250 cycles. That is conveniently close to the binary number 256, and this preferred embodiment is arranged so that it will turn off automatically after having completed an exercise program of 256 cycles.

It has also been discovered that the muscle contraction and relaxation times are sufficiently slow so that it is not necessary that energy be supplied continuously to the rings 16 and 18 during the on portion of the pulse cycle. The invention takes advantage of that fact by forming the two-second on pulse as a series of higher frequency pulses. Pulse amplitude is not changed. Instead, the energy in the two-second pulse is varied wherby to control the degree of muscle of contraction by altering the relative on and off times of the higher frequency pulses that form the two-second on pulse. A preferred circuit form by which these several features of the invention may be accomplished is depicted in FIG. 4.

Circuit Description

In addition to the metal energizing rings 16 and 18, and the intensity control surfaces 20, 22 and 24, the circuit diagram depicted in FIG. 4 includes a combined clock and counter unit 50, a comparator 54, an up-/down counter 56, a counter 58, a four-input AND gate 60, another four-input AND gate 62, a four-input NOR gate 64, an OR gate 66, another OR gate 68, a NOR gate 70, a field effect switching transistor 72, an inverter of the kind that is subject to internal hysteresis 74, a similar inverter 76, an iron core inductor 78, and a number of additional circuit elements.

At the upper left, in FIG. 4, resistors 80 and 82 and capacitor 84 are connected from a common point to pins 11, 10 and 9, respectively, of the clock counter unit 50. Those three elements determine the operating frequency of the internal clock of unit 50. Pins 8 and 16 are connected to ground and positive supply potential, respectively. The reset pin 12 of the clock counter 50 is connected to the output of OR gate 68. Pins 13 and 14 are connected to two of the inputs of AND gate 60. A third input of the AND gate is connected to the output of OR gate 66, the two inputs of which are connected to pins 12 and 3, respectively, of the comparator 54. Pins 7, 5, 4 and 6 of the clock counter 50 are connected to pins 10, 7, 2 and 15, respectively, of the comparator 54. Pin 16 of the comparator is connected to the positive supply line, and pin 8 is connected ro ground. The output of the clock counter 50 appears at pin 3 which is connected to pin 10 of counter 58. Pin 16 and 8 of the latter are connected to the positive supply line and to ground, respectively. Pin 5 of counter 58 is connected to the fourth input of the AND gate 60. The output of that gate is applied to the gate of the field effect transistor 72. The upper input of OR gate 68 is connected to pin 1 of counter 58. Pin 11 of the counter is connected to the lower input of OR gate 68. It is connected through a capacitor 86 to the positive supply line and through a resistor 88 to the output of NOR gate 70. That NOR gate has four inputs tied together in pairs. One pair is connected to pin 5 of counter 58. The other pair is connected through a resistor 90 to the contact ring 18 and to ground through the parallel combination of a resistor 92 and a diode 94. The drain of transistor 72 is connected to energizing ring through capacitor 98 and to one end of the iron core coil 78. The other end of the coil is connected through a capacitor 96 to ground, to the positive supply line and to the energizing ring 16. A discharge resistor 100 is connected in parallel with the core 78.

The circuit thus far described generates and supplies the contraction inducing energy to the rings 16 and 18. It senses and turns on the energizing section upon insertion, and it senses and rurns off the energizing section upon removal of the instrument. The remainder of the circuit is devoted to control of the level of energy supplied to the energizing rings 16 and 18.

The energy level control system includes connections from pins 11, 9, 1 and 14 of the comparator 54 to pins 3, 2, 6 and 7, respectively, of the up/down counter 56. Pins 11 and 16 of the latter are connected to the positive supply line. Pins 8, 15, 1, 10, 9 and 14 are connected together to ground and the negative side of the supply source. The output of OR gate 104 is connected to count up pin 5 of the counter 56. The output of OR gate 106 is connected to the count down pin 4. One input of the OR gate 104 is connected to the intensity control surface 24 through the series combination of inverter 74, resistor 108, and a diode 110. One input of gate 106 is connected to the intensity control surface 20 through the series combination of the inverter 76, a resistor 112, and a diode 114. The junction between the inverter 74 and resistor 108 is connected to ground through the parallel combination of a capacitor 116 and a resistor 118. On the down side, the junction between the inverter 76 and resistor 112 is connected to ground through the parallel combination of a capacitor 120 and a resistor 122. The four pins 3, 2, 6 and 7 of the up/down counter 56 are connected to the four input of NOR gate 64 and to the four inputs of AND gate 62. The output of AND gate 62 is connected to the other input of OR gate 104, and the output of the NOR gate 64 is connected to the other input of OR gate 106. The bartery is designated by the reference numeral 124, and it is connected between the positive supply line and ground. The common control surface 22 is connected to the positive supply line.

In the preferred embodiment of the invention, the clock counter 50 is an integrated circuit type CD4060CBM. Counter 58 is an integrated circuit type MC14040B. The comparator is an integrated circuit type 74C85. The up/down counter 56 is an integrated circuit type CD401938C. Gate 60 is one half, and gate 62 is the other half of an integrated circuit type MC14082B. NOR gates 64 and 70 are packaged together in an integrated circuit type CD40028C. OR gates 66, 68, 104 and 106 are packaged together in an integrated circuit type MC14071B. The rwo inverters 74 and 76 are two of six that are packaged together in an integrated circuit type 74C914. The transistor is type VN10KM. The resistors and capacitors in the circuit have the following values:

| Resistor | Value | Capacitor | Value |
| --- | --- | --- | --- |
| 80 | 300 k ohms | 84 | 47 pf |
| 82 | 100 k ohms | 86 | .01 mfd |
| 88 | 1 meg ohm | 96 | 47 mfd |
| 90 | 100 k ohms | 98 | 1 mfd |
| 92 | 47 k ohms | 116 | 1000 pf |
| 100 | 510 k ohms | 120 | 1000 pf |
| 108 | 100 k ohms | | |
| 112 | 100 k ohms | | |
| 118 | 15 meg ohms | | |
| 112 | 15 meg ohms | | |

The battery 124 supplies a porential of 9 volts. In the preferred form of the invention, the battery is rechargeable, and it can be recharged by connecring the charger across the excitation rings 16 and 18. ring 16 is connected to the positive supply line. The other ring 18 is connected to the cathode of diode 94 whose annode is connected to ground. When the external battery charger is connected across rings 16 and 18, the diode 94 will be forward biased and will permit charging current to flow into the battery. The potential from ring 18 to ground will be the forward voltage drop across the diode 94. That voltage drop applied through resistor 90 to gate 70 will maintain the gate input at a logic low to ensure that the clock in clock counter 50 will not generate pulses during charging of the battery.

Circuit Operation

When the instrument is in operation, a high at the output of AND gate 60, being applied to the gate of the transistor 72, will cause the transistor to be turned on for the period of the output pulse. Current from the positive supply line flows through the inductor 78 and the transistor 72. During the period of conduction, energy will be stored in the field surrounding the inductor. At the end of the pulse that field will collapse, generating a counter-electromotive force in the inductor coil. The transistor 72 having been rendered non-conductive, the energy of the coil is discharged through the circuit formed by capacitor 98 and the resistance of the tissue that bridges energization rings 16 and 18.

In this embodiment, the muscle contraction period is to be two seconds long, followed by a relaxation period of two seconds. The contraction energy is furnished in a series of fifteen pulses which are counted by counter 58. In this embodiment, the muscle exercise program continues through 256 muscle contractions and then stops. Operation is initiated when the energizing rings are bridged by tissue. The circuit having been initiated, a series of fifteen pulses will appear at the output of gate 60 followed by a period equal to the duration of fifteen pulses when the output of gate 60 will remain low. In this embodiment, two seconds will have elapsed during the generation of the fifteen high signals at the o tput of gate 60. That is followed by a two-second period in which the output of gate 60 remains low. That cycle of operation will be repeated 265 times, the count being made in counter 58.

The frequency of the pulses is controlled by the clock in clock counter 50, a:d in this embodiment is 32 kHz. The magnitude of high signal at the output of gate 60 does not change. What does change to vary the amount of energy supplied to the tissue bridging the excitation rings 16 and 18 is the width of the outpur pulses at gate 60. Pulse width is controlled by a combination of up/-down counter 56 and the comparator 54.

The AND gate 60 has four inputs. Two are connected to pins 13 and 14 of the clock counter 50. These inputs determine the period of the output pulses from the AND gate 60. That period is determined by clock frequency and the counter serving as a divider. The duration of that portion of the period over which the AND gate is turned on is determined by the output of OR gate 66. A digital number from 1 to 15 is applied by the up/down counter 56 to pins 11, 9, 1 and 14 of the comparator unit 54. That digital number is compared with the current count in counter 50 which appears on pins 7, 5, 4 and 6. As long as the current count is equal to or less than the digital number applied by the up/-down counter 56, the OR gate 56 will be turned on, but when the current count exceeds that number, it will be turned off. By changing the digital number applied to pins 11, 9, 1 and 14, the length of the pulse on period is changed. Fifteen different numbers can be applied by the four lines that connect to those pins so that it is pos--ible to alter the width of the OR gate 66 output in fifteen steps. The higher the digital number, the greater the width of the OR gate output pulse.

The up/down counter 56 is not connected to the clock. It will count up one for each pulse that is applied to the count up input at pin 5, and it will count down one pulse for each input that is applied at the count down input at pin 4. The count signal in each case is applied through an OR gate, OR gate 104 in the case of pin 5 and OR gate 106 in the case of pin 4. The digital number that is applied to the comparator unit 54 appears at pins 3, 2, 6 and 7 of the up/down counter. The signal it each of those pins is applied to an associated one of the inputs of AND gate 62. When the count goes full, so that all of the gate inputs are high, the output of gate 62 will go high whereupon the output of OR gate 104 will go high whereupon pin 5 of the up/down counter will go high, and furrher up counting will be prevented. Pins 3, 2, 6 and 7 of the up/down counter are also connected to the four inputs of the NOR gate 64 the output of which goes high when the up/down counter count is reduced to zero. When the output of the NOR gate goes high, a high will be applied to one of the inputs of OR gate 106, and the output of that OR gate and pin 4 will go high so that further down counting will be prevented. In input signal to the up counter pin 5 is applied by simultaneously touching the intensity control surfaces 22 and 24. Doing that will apply a positive voltage through the resistance, or dielectric, of the user's finger to the diode 110 and resistance 108 and the inverter 74, to the other input of OR gate 104. Applying the positive signal to the input of gate 74 results in a low at its output. Unless the count is full, and the AND gate output is high, applying a low to the input of gate 104 will result in a low being applied to up count input 5, and the counter will advance one digital number. On the other hand, if the intensity control surfaces 22 and 20 are bridged by the user's finger a positive signal will be applied to the input of inverter 76 through rhe combination of diode 114 and resistor 112. That will result in a low appearing at the output of the inverter and a low being applied to the input of OR gate 106. If the other input is low because the output number of the up/down counter is other than zero, then the output of the OR gare 106 will be low and that low, applied to pin 4, will result in a down count of one digital number.

When the instrumenr is not in use, when the excitation rings 16 and 18 are not bridged by the resistance of tissue, the ring 18 will be at a low potential. That low will be applied to the input of NOR gate 70 through resistor 90. Initially, the counter 58 will be reset so that a low is also applied from pin 5 at counter 58 to the other input of NOR gate 70. In that circumstance, the output of the NOR gate 70 is a high, and that high, applied through resistor 88 to the reset pin 11 of counter 58 and to the upper input of OR gate 68 and, consequently, a high signal at the reset input 12 of clock counter 50, will result in both of the counters held in the reset condition. In that condition, the clock in unit 50 is stopped and, because these devices use the CMOS or other construction in which the quiescent current drain is negligible, virtually no power is consumed in the system. If the excitation rings 16 and 18 are bridged by a tissue, a voltage divider will be formed in the circuit that extends from the positive supply line through ring 16, the tissue, ring 18, and resistor 92 to ground. The effect of that will be to list the potential of ring 18 to the point at which it represents a logic high when applied to the upper input of NOR gate 70 through resistance 90. When that occurs, the output of the NOR gate will go low, and that signal, applied through resistor 88 to the reset pin 11 of counter 58, will enable that counter. The low output of the NOR gate is also applied through the resistor 88 to the upper input of OR gate 68 whereupon the output of the OR gate 68 will go low to enable the clock counter 50, and the operation previously described will be initiated and continue. It will continue until the counter 58 reaches full count at the digital number 256, in this embodiment. At that point, the output at pin 1 of counter 58 will go high. That output is applied to the lower input of OR gate 68 and will be applied to the reset pin 12 of the clock counter 50 whereupon the clock will stop and the system will return to quiescense. It will remain in the quiescent state until the resistance bridge across rings 16 and 18 is removed and the upper input of the NOR gate 70 is returned to a logic low.

A provision is incorporated which forces the operation to continue, notwithstanding removal of the bridge across rings 16 and 18 until the fifteen counts of the current two-second energizing pulse period has ended. Pin 5 of counter 58 is connected to one of the inputs of AND gate 60 and is also connected to the lower input of the NOR gate 70. Until the count reaches 15, the output of pin 5 will remain high to permit output pulsing at gate 60, and it will maintain the lower input of NOR gate 70 high so that the output of the NOR gate is a low and resetting of the counter 58 and the clock counter 50 is prevented until the count reaches 15.

SUMMARY OF FEATURES

The invention and apparatus which embodies the invention incorporate some, or all, of the features in the following list which is not, and is not intended to be, exhaustive.

(1) A total exercise program can be incorporated in the instrument.

(2) Contraction intensity can be changed manually.

(3) Intensity change can be made at any time whether or not the instrument is in use.

(4) Intensity level is remembered even in the quiescent state.

(5) The instrument automatically reverts to quiescent state when removed from use, and "wakes up" to full power and remembered intensity level, automatically, when placed in use.

(6) No moving elements are required.

(7) Completely sealed construction permits full immersion for cleaning.

(8) Battery power is sufficient and batteries can be recharged.

(9) Intensity change is accomplished by pulse width change.

(10) Intensity change is possible without change in duration of contraction time or signal processing potentials.

(11) Fail-safety ensures against possibility of shock.

(12) The exercise program automatically resets upon removal from use.

(13) Physician can prescribe a specific program in quantitative terms which both physician and patient understand, and which the patient can follow.

(14) Electronic design configuration requires no temperature compensation or bubble or bounce protection, or response race problem.

(15) Functional operation can be achieved with separate solid state devices as in the preferred embodiment or an integrated device, or devices, or in a microprocessor.

(16) Functional operation can be achieved in full or in part to accommodate other exercise programs that the preferred program describes above.

(17) Package and switch configuration permits full control by the patient of degree of insertion, intensity of contractions, and, by removal at any time, of the length of the exercise program.

(18) Abbreviated exercise programs can be defined as number of contractions, or as a period of insertion.

Although I have shown and described certain specific embodiments of my invention, I am fully aware that many modifications thereof are possible. My invention, therefore, is not to be restricted except insofar as is necessitated by the prior art.

I claim:

1. An electric muscle contraction inducer comprising a cylindrical housing having reduced diameter at the forward end along its length and a pair of energizing electrodes carried at spaced points along said forward end at which energizing signals appear in operation and having at its rearward end control means responsive to touch for initiating change in the amount of energy in said signals;

said control means comprising at least three surfaces electrically insulated each from the others and responsive when a first and second of said surfaces are touched simultaneously by the user to initiate an energy increase and when the second and third of said surfaces are touched simultaneously by the user to initiate an energy decrease; and at least said first and third surfaces being disposed on the rearward face of said instrument.

2. The invention defined in claim 1 which further comprises contraction energy means for supplying electrical energy to said electrodes during succession of energizing intervals separated by non-energizing intervals in which no energy is supplied to said electrodes.

3. The invention defined in claim 2 in which said control means is responsive to touch for initiating a change in the width of said pulses.

4. The invention defined in claim 2 in which said contraction energy means is effective to furnish energy over a pre-established number of energizing intervals provided than an energy absorbing load is connected to said electrodes for the period of said number of intervals.

5. The invention defined in claim 2 which further comprises means for rendering said contraction energy means effective for supplying energy upon said electrodes being bridged by tissue and for terminating the supply of energy to said electrodes when not bridged by tissue.

6. The invention defined in claim 3 in which said contraction energy means comprises an energy storage element arranged to discharge energy to said electrodes and means responsive to each pulse of said series of pulses to store energy in said energy storage element;

said pulse generating means comprising a clock pulse generating clock, and a first counter connected to count clock pulses and to furnish count signals to a second counter, and a third counter for supplying a selected count signal, and a comparator for comparing the count in said first counter with the selected count signal and furnishing a comparison signal upon occurance of a predetermined state of comparison and pulse width altering means including a gate responsive to supply pulses to said energy supply means the width of which pulses is a joint function of a count signal in said first counter and said comparison signal.

7. The invention defined in claim 6 in which said third counter comprises means responsive to touch to cause said third counter to change the count signal furnished to said comparator.

8. The invention defined in claim 2 in which said contraction energy means is effective to supply energy as a succession of pulses during said energizing intervals.

* * * * *